United States Patent [19]
Kenet

[11] Patent Number: 5,241,468
[45] Date of Patent: Aug. 31, 1993

[54] APPARATUS AND METHOD FOR SPECTRAL ENHANCEMENT OF BODY-SURFACE IMAGES TO IMPROVE SENSITIVITY OF DETECTING SUBTLE COLOR FEATURES

[75] Inventor: Robert O. Kenet, Lakeland, Fla.

[73] Assignee: Vanguard Imaging Ltd., Cambridge, Mass.

[21] Appl. No.: 606,657

[22] Filed: Oct. 31, 1990

Related U.S. Application Data

[63] Continuation-in-part of Ser. No. 509,039, Apr. 13, 1990, which is a continuation-in-part of Ser. No. 337,304, Apr. 13, 1989, Pat. No. 5,016,173.

[51] Int. Cl.⁵ .......................................... G06F 15/42
[52] U.S. Cl. ................................. 364/413.01; 382/6
[58] Field of Search ................ 364/413.01, 413.13; 382/6; 128/653 R

[56] References Cited

U.S. PATENT DOCUMENTS 4,183,046  1/1980  Dalke et al. ......................... 358/22

*Primary Examiner*—Gail O. Hayes
*Attorney, Agent, or Firm*—Iandiorio & Dingman

[57] ABSTRACT

A method for spectrally-enhancing images of a body surface includes the step of increasing the Saturation values of each pixel in the image. The methods increase the sensitivity with which a human observer can detect certain reflected wavelengths. Where the body surface is skin, for example, the method can be used to detect melanoma or other conditions where there is a deep dermal pigment characterized by a visible blue backscatter, or to detect the visible red backscatter characteristic of erythema. Also, apparatus for spectrally-enhancing images of a body surface includes means for color imaging the surface, means for increasing the saturation of the color in that image, and means for displaying the color-saturated image.

13 Claims, No Drawings

APPARATUS AND METHOD FOR SPECTRAL ENHANCEMENT OF BODY-SURFACE IMAGES TO IMPROVE SENSITIVITY OF DETECTING SUBTLE COLOR FEATURES

This application is a continuation-in-part of copending U.S. application Ser. No. 509,039, filed Apr. 13, 1990, titled "Apparatus and Method for Monitoring Surfaces of the Body," which is a continuation-in-part of copending U.S. application Ser. No. 337,304, U.S. Pat. No. 5,016,173 filed Apr. 13, 1989, titled "An Improved Apparatus and Method for Monitoring Visually Accessible Surfaces of the Body" (issue fee paid Jul. 24, 1990).

BACKGROUND OF THE INVENTION

This invention relates to an improvement in the apparatus and method for monitoring surfaces of the body disclosed in copending applications Ser. Nos. 509,039 and 337,304, which are hereby incorporated by reference. The invention particularly relates to preprocessing of images as described on pages 26-29 of Ser. No. 509,039 and on pages 22-24 of Ser. No. 337,304, U.S. Pat. No. 5,016,173 and more particularly to color transforms of images as described therein.

SUMMARY OF THE INVENTION

The invention is a method and apparatus for spectrally-enhancing a color image, particularly when adapted for monitoring a region of a surface of a person's body, the method including recording a color image of the region, increasing the Saturation value of each pixel in a Hue-Saturation-Intensity (H-S-I) representation of the image, and displaying the resulting spectrally-enhanced image.

The recorded image may be a non-H-S-I color image, in which case the methods include the step of transforming the non-H-S-I image to an H-S-I image. Further, the displayed image may be a non-H-S-I image, in which case the methods include the step of transforming the spectrally-enhanced H-S-I image to a non-H-S-I image.

Conventional recording devices operate in the Red-Green-Blue (R-G-B) color space, and in preferred embodiments, the recorded image is R-G-B and the methods include the step of transforming the R-G-B image to an H-S-I image. Conventional printers and monitors also operate in the R-G-B color space, and in preferred embodiments, the displayed image is R-G-B and the methods include the step of transforming the spectrally-enhanced H-S-I image to an R-G-B image.

The methods of the present invention can optionally further include the steps either of histogram equalizing the Intensity values or of increasing the Intensity values.

In one aspect, the method is used for monitoring a skin region. The methods of the present invention spectrally-enhance the acquired image to emphasize visible blue backscatter from skin and can be used to detect deep dermal pigment which may represent melanoma. The methods of the present invention also spectrally-enhance the acquired image to emphasize visible red backscatter from skin and can be used to detect erythema in a pigmented skin lesion.

DESCRIPTION OF THE PREFERRED EMBODIMENT

The invention features an image manipulation technique which can be used to enhance or extract selected image attributes. Appropriate hardware and software for implementing the methods are disclosed in the above-cited copending applications, which have been incorporated by reference. The method of the invention can be applied to either digital or analog images.

According to one embodiment of the method of the invention, a color camera is used to image a surface such as a body surface. The image is preferably acquired according to the techniques of oil-immersion epiluminescence microscopy as discussed in copending application U.S. Ser. No. 509,039 and as used in dermatology. The camera is preferably a 3-chip Red-Green-Blue (R-G-B) video camera. An acquired image is transformed from the R-G-B color space (or other input color space) to any type of Hue-Saturation-Intensity (H-S-I) space using a color transform. If a variant of the H-S-I color space model is used, such as those variations which are also based on human perception of color, e.g., the H-S-V (Value) space, the H-S-B (Brightness) space, the H-S-L (Lightness or Luminence) space, or any other, then the appropriate parameter such as Value, Brightness, Lightness, or Luminence may be substituted for Intensity.

According to the methods of the present invention, the Saturation for each image pixel is increased. This results in a spectral enhancement which emphasizes image attributes. In preferred embodiments, the Saturation for each pixel is set to 100%.

The spectrally-enhanced image is preferably displayed on an R-G-B monitor or printer after the H-S-I image is transformed to an R-G-B image.

In addition to increasing the Saturation for each image pixel, optionally, a histogram equalization can be performed on the Intensity values, or the Intensity value at each pixel can be increased (preferably set to its maximum possible value, i.e., 256 for an 8-bit system).

The image resulting from the maximization of Saturation represents a color or spectral enhancement of the light reflected from the surface. The enhancement effectively changes the spectrum of light perceived to have been reflected from each pixel region from one approximating "true-color" to one where the new color is (within a certain error bound which may be large) the predominant wavelength of the spectrum of light reflected by that pixel region displayed at maximum saturation. In effect, the manipulation narrows the spectral bandwidth to a spike approximately at the wavelength of the predominant wavelength of reflected light. This increases the human observer's sensitivity to detecting hues (wavelengths) reflected from the surface. Any increase in the Saturation values may improve the observer's sensitivity. The greater the increase the greater the enhancement, and the observer's sensitivity may be maximized if the Saturation is increased to 100%.

Applied to the human skin surface, the method increases the sensitivity with which a human observer can detect certain reflected wavelengths. Normal skin containing predominantly melanin should look brown, yellow, or orange, whereas skin with more hemoglobin may look red, and whereas deep dermal pigment may look blue ("Tyndall effect") in an image which has been spectrally enhanced by maximizing the Saturation of each pixel to 100% while not changing the hue of each pixel. This is useful, for example, for enhancing the visible blue backscatter often seen in melanoma or other conditions where there is a deep dermal pigment. It may also be useful for easily detecting erythema. Regions of skin containing connective tissue, which causes more blue backscattering, will be blue if enough pigment is below it to absorb the deeper penetrating red light, or magenta/purple if the blue backscattering is combined with the red reflectance of hemaglobin/blood.

What is claimed is:

1. A method for visualizing a region of a surface of a person's body, to assist in detection of anatomic features or abnormalities, comprising:
   capturing an image of the region;
   producing a color space representation based on hue and saturation, of the captured image of the region;
   increasing the saturation of the representation, while keeping the hue constant; and
   displaying or printing the saturation-increased representation.

2. The method of claim 1 in which capturing an image includes recording an R-G-B representation of an image of the region.

3. The method of claim 2 in which producing a color space representation includes transforming the R-G-B representation into an H-S-I representation of the image.

4. The method of claim 3 wherein the Saturation value of each pixel in the H-S-I representation of the image is increased to 100%.

5. The method of claim 3 further comprising the step of histogram equalizing the Intensity values in the H-S-I representation of the image.

6. The method of claim 3 further comprising the step of increasing the Intensity value of each pixel in the H-S-I representation of the image.

7. The method of claim 6 wherein the Intensity value of each pixel in the H-S-I representation of the image is increased to the maximum value.

8. The method of claim 2 in which recording an R-G-B representation includes recording a color image of the body surface.

9. The method of claim 8 the color image of skin having been obtained according to the techniques of oil-immersion epiluminescence microscopy.

10. Apparatus for visualizing a region of a surface of a person's body, to assist in detection of anatomic features or abnormalities, comprising:
    means for capturing an image of the region;
    means for producing a color space representation, based on hue and saturation, of the captured image of the region;
    means for increasing the saturation of the representation while keeping the hue constant; and
    means for displaying or printing the saturation-increased representation.

11. The apparatus of claim 10 in which said means for producing a color space representation includes means for recording an R-G-B representation of an image of the region.

12. The apparatus of claim 11 in which said means for producing a color space representation includes means for transforming the R-G-B representation into an H-S-I representation of the image.

13. The apparatus of claim 12 in which said means for increasing the saturation includes means for increasing the saturation of each point in the representation to 100%.

* * * * *